US012588690B2

(12) United States Patent  
Asaro et al.

(10) Patent No.: US 12,588,690 B2  
(45) Date of Patent: Mar. 31, 2026

(54) NET ENERGY MODEL FOR COMPANION ANIMALS AND METHODS

(71) Applicant: MARS, INCORPORATED, McLean, VA (US)

(72) Inventors: Natalie Julia Asaro, Guelph (CA); Wilfredo Daniel Mansilla Tafur, Guelph (CA); David John Seymour, Guelph (CA); John Paul Cant, Guelph (CA); Anna Katharine Shoveller, Guelph (CA)

(73) Assignee: Mars, Incorporated, McLean, VA (US)

( * ) Notice: Subject to any disclaimer, the term of this patent is extended or adjusted under 35 U.S.C. 154(b) by 1067 days.

(21) Appl. No.: 17/250,033

(22) PCT Filed: May 9, 2019

(86) PCT No.: PCT/US2019/031560  
§ 371 (c)(1),  
(2) Date: Nov. 9, 2020

(87) PCT Pub. No.: WO2019/217707  
PCT Pub. Date: Nov. 14, 2019

(65) Prior Publication Data  
US 2021/0251259 A1 Aug. 19, 2021

Related U.S. Application Data

(60) Provisional application No. 62/668,906, filed on May 9, 2018.

(51) Int. Cl.  
B65B 61/02 (2006.01)  
A01K 5/00 (2006.01)  
(Continued)

(52) U.S. Cl.  
CPC ................ A23K 50/42 (2016.05); A01K 5/00 (2013.01); A01K 29/00 (2013.01); B65B 1/04 (2013.01);  
(Continued)

(58) Field of Classification Search  
CPC ............................... G16H 20/60; A23K 50/42  
See application file for complete search history.

(56) References Cited

U.S. PATENT DOCUMENTS 6,681,717 B2 1/2004 Burghardi et al.  
7,152,036 B2 12/2006 Gizzio  
(Continued)

FOREIGN PATENT DOCUMENTS

JP 2009-72157 A 4/2009  
JP 2010-163424 A 7/2010  
(Continued)

OTHER PUBLICATIONS

Castrillo et al., Methods for predicting the energy value of pet foods, Jul. 2009, Revista Brasiliera de Zootecnia 38: 1-14 (Year: 2009).*  
(Continued)

*Primary Examiner* — Jesse P Frumkin  
*Assistant Examiner* — Theodore Charles Striegel  
(74) *Attorney, Agent, or Firm* — Morrison & Foerster LLP

(57) ABSTRACT

A model for predicting the net energy available to a companion animal from a pet food is provided. The model can be used to determine the appropriate amount of a food to feed a companion animal, and/or to provide feeding guidelines for any type of food, for any companion animal, and such methods are provided. Also provided are methods of packaging food for a companion animal, animal, and methods of maintaining a desired weight, or effecting weight loss, in a companion animal.

3 Claims, 1 Drawing Sheet

(51) Int. Cl.
*A01K 29/00* (2006.01)
*A23K 50/42* (2016.01)
*B65B 1/04* (2006.01)
*G16H 20/60* (2018.01)
*G16H 50/00* (2018.01)

(52) U.S. Cl.
CPC ........... *B65B 61/025* (2013.01); *G16H 20/60* (2018.01); *G16H 50/00* (2018.01)

(56) References Cited

U.S. PATENT DOCUMENTS

| | | | |
|---|---|---|---|
| 2008/0149039 A1 | 6/2008 | Willcocks et al. | |
| 2008/0234995 A1 | 9/2008 | Newcomb et al. | |
| 2016/0324188 A1 | 11/2016 | Johnston et al. | |

FOREIGN PATENT DOCUMENTS

| | | | | |
|---|---|---|---|---|
| WO | 2015/155177 A1 | 10/2015 | | |
| WO | WO-2016130981 A1 * | 8/2016 | ............. | A23K 10/20 |
| WO | 2019/217707 A1 | 11/2019 | | |

OTHER PUBLICATIONS

Moehn et al., Using Net Energy for Diet Formulation: Potential for the Canadian Pig Industry, 2005, Advances in Pork Production 16 : 119-129 (Year: 2005).*

Leblanc et al., Effect of meal size and frequency on postprandial thermogenesis in dogs, Feb. 1986, American Journal of Physiology 250(2): 144-147 (Year: 1986).*

'AAFCO Pet Food Regulations Label Review Checklist', AAFCO/PFI Pet Food Workshop, Nashville TN, Aug. 2008 (Year: 2008).*

Fomby, 'Scoring Measures for Prediction Problems', Department of Economics, Southern Methodist University, Jun. 2006 (Year: 2006).*

Hashimoto et al., Characteristic Relation between Dietary Metabolizable Energy Content and Digestible Energy Content in Laboratory Cats, Experimental Animals 44(1): 23-28, 1995 (Year: 1995).*

National Research Council, Nutrient Requirements of Dogs and Cats, The National Academies Press, pp. 28-45, 2006 (Year: 2006).*

Mochn et al. (2005). "Using Net Energy for Diet Formulation: Potential for the Canadian Pig Industry" Advances in Pork Production, vol. 16., pp. 119-129.

Asaro et al. (2018). "Modelling net energy of commercial cat diets", located at https://atrium.lib.uoguelph.ca/xmlui/handle/10214/12926?show=full; (24 pages).

Hall et al. (Jan. 2013). "Using Gross Energy Improves Metabolizable Energy Predictive Equations for Pet Foods Whereas Undigested Protein and Fiber Content Predict Stool Quality", Plos One, 8(1). 8 pages.

Noblet et al. (Dec. 2014). "Prediction of Net Energy Value of Feeds for Growing Pigs", J. Anim. Scl., Feb. 1994, 72:344-354.

Asaro et al.(Nov. 2017). "Digestibility is Similar between Commercial Diets That Provide Ingredients with Different Perceived Glycemic Responses and the Inaccuracy of Using the Modified Atwater Calculation to Calculate Metabolizable Energy" Veterinary Sciences 4(54);12 pages.

Anonymous, The Association of American Feed Control Officials (AAFCO), Calorie Content, retrieved from the Internet: URL:https://petfood.aafco.org/Calorie-Content, Jan. 1, 2012, 3 pgs.

Case et al., "Energy and Water + Energy Balance," Canine and Feline Nutrition—Resource for Companion Animal Professionals, Mosby Elsevier, 31 pgs., Jan. 1, 2011.

Anonymous, "Chapter 3: Calculation of the Energy Content of Foods—Energy Conversion Factors," FAO Food and Nutrition Paper 77—Food energy methods of analysis and conversion factors Report of a Technical Workshop, Rome, Dec. 2002, pp. 1-20.

International Search Report and Written Opinion, dated Jul. 5, 2019 for International Application No. PCT/US2019/031560, filed on May 9, 2019, 16 pgs.

* cited by examiner

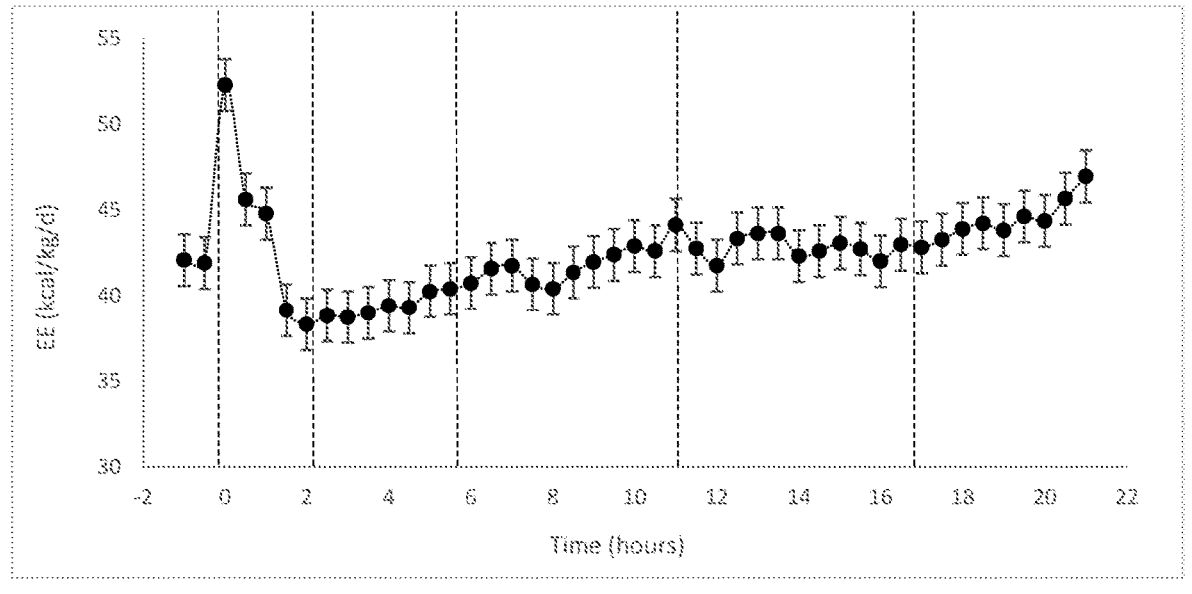

<table>
<tr><td>1</td><td>2</td></tr>
</table>

NET ENERGY MODEL FOR COMPANION ANIMALS AND METHODS

CROSS REFERENCE TO RELATED APPLICATIONS

This application is a national stage application filed under 35 U.S.C § 371 of International Application No. PCT/US2019/031560 filed on May 9, 2019, which claims priority to U.S. Provisional Application No. 62/668,906, filed on May 9, 2018, for which the entire contents of each are hereby incorporated by reference in their entirety.

FIELD

A model for predicting the net energy available to a companion animal from a pet food is provided. The model can be used to determine the appropriate amount of a food to feed a companion animal, and/or to provide feeding guidelines for any type of food, for any companion animal, and such methods are provided. Also provided are methods of packaging food for a companion animal, and methods of maintaining a desired weight, or effecting weight loss, in a companion animal.

BACKGROUND

Most pet owners feed their pets commercially prepared pet foods. In order to determine how much food to feed, one must know the energy density of the food. One way of expressing the energy density of a food is metabolizable energy (ME). Metabolizable energy is understood in the art to mean digestible energy (DE), which is equal to gross energy minus energy lost in feces and urine, and gaseous products of digestion.

The most accurate method of determining the digestible energy or metabolizable energy of a food product, in turn, is through animal feeding studies. Because such feeding studies can be costly and time consuming, generally accepted Atwater equations, or modified Atwater equations, are used to predict metabolizable energy values of pet foods. Both the traditional and modified Atwater equations assign coefficients for the three macronutrients: protein, carbohydrate and fat. Pet food industry standards currently use the modified Atwater equation to estimate the metabolizable energy of pet foods.

Whether traditional or modified, the same Atwater formula is used irrespective of the companion animal being fed and neither the traditional or nor the modified Atwater equation account for relative fiber content or presumed digestibility. As a result, calculations using either tend to underestimate the energy content of highly digestible foods and overestimate those of less digestible foods. The Atwater equations are thus not considered to accurately predict the metabolizable energy value of pet foods, at least because of this deficiency. There is additionally a perception in the art that the assigned macronutrient coefficients are unreliable.

Research has thus been conducted in efforts to identify more accurate models to estimate the energy content of foods. For example, the National Research Council has suggested that a more accurate model for predicting metabolizable energy involves accounting for crude fiber and digestability of energy. Others have proposed taking into account the amino acid and non-amino acid compounds in the crude protein fraction to better predict metabolizable energy.

More effective and accurate models of predicting the energy content of food for companion animals are thus needed in the art, as underestimation of the energy content results in inaccurate feeding recommendations, which in turn, can result in overfeeding, and contribute to obesity and its associated disorders.

SUMMARY

It has now been surprisingly discovered that net energy can be a more accurate measure of energy directly available to a companion animal upon ingesting a food than metabolizable, direct, or gross energy, and models are provided herein for predicting the net energy of a food. The models for estimating net energy provided can be used to accurately predict the net energy available to a companion animal after ingesting a food, and the net energy in turn used to provide more accurate feeding guidelines than may currently be provided based upon metabolizable energy models. Of additional benefit is that the provided models to predict net energy are based upon a lower number of parameters than are required in either the traditional or modified Atwater equation. The model(s) provided are thus not only more accurate than conventional models of predicted metabolizable energy, but are also simplified compared to such existing models.

In a first aspect, a model for predicting the net energy available to a companion animal after ingesting a food is provided. The model consists of the heat increment of feeding the food, expressed as a proportion of metabolizable energy, and one macronutrient input. The macronutrient input may be crude protein (CP), crude lipids (CL), starch or crude fiber (CF), and in some instances, is desirably crude protein (CP). The companion animal may be a cat, and in such embodiments, the model may be one of net energy= $(0.941\times$ metabolizable energy$)+(0.519\times$ crude protein); net energy=$(0.992\times$ metabolizable energy$)-(0.170\times$ CL); net energy=$(0.995\times$ metabolizable energy$)-(0.0002\times$ starch); net energy=$(0.984\times$ metabolizable energy$)+(0.246\times$ crude fiber); net energy=$(0.605\times$ metabolizable energy$)+(2.60\times$ crude protein); net energy=$(0.843\times$ metabolizable energy$)-(0.431\times$ crude lipids); net energy=$(0.826\times$ ME$)-(0.0001\times$ starch); or net energy=$(0.800\times$ metabolizable energy$)+(6.386\times$ crude fiber). Of these, net energy=$(0.941\times$ metabolizable energy$)+(0.519\times$ crude protein); net energy=$(0.992\times$ metabolizable energy$)-(0.170\times$ crude lipids); net energy=$(0.995\times$ metabolizable energy$)-(0.0002\times$ starch); net energy=$(0.984\times$ metabolizable energy$)+(0.246\times$ crude fiber) are particularly accurate, and preferred and net energy=$(0.941\times$ metabolizable energy$)+(0.519\times$ crude protein) is most preferred.

Because net energy is believed to be a more accurate prediction of the energy actually available to a companion animal after ingesting a food than metabolizable energy, using net energy instead of metabolizable energy to provide feeding guidelines for companion animals is expected to provide more appropriate feeding guidelines. And so, in another aspect, a method of providing feeding guidelines for a food for a companion animal are provided. The method comprises predicting the net energy provided by the food using a model consisting of the heat increment of feeding the food, expressed as a proportion of metabolizable energy, and one macronutrient input and multiplying the predicted net energy by the energy requirement for the companion animal. In some embodiments, the companion animal may be a cat, in which case, the macronutrient input may be crude protein and the model may be net energy=$(0.941\times$ metabolizable energy$)+(0.519\times$ crude protein).

Use of net energy, instead of the industry standard of Metabolizable energy, has now been learned to result in the provision of more appropriate feeding guidelines, and this advantage may be further leveraged by providing the same in conjunction with the companion animal food. And so, in an additional aspect, a method of packaging a food for a companion animal is provided. The method comprises providing a food for a companion animal and packaging therefor. The net energy provided by the food when consumed by the companion animal is predicted using a model consisting of the heat increment of feeding the food, expressed as a proportion of metabolizable energy, and one macronutrient input. The predicted net energy is then multiplied by the energy requirement for the companion animal to provide feeding guidelines for the food for the companion animal. The so determined feeding guidelines are printed on the package, and the food packaged in the printed package.

The provision of more appropriate feeding guidelines can deter or prevent overfeeding of companion animals, and methods of doing the same are also provided. The method comprises predicting the net energy provided by a food for a companion animal using a model consisting of the heat increment of feeding the food, expressed as a proportion of metabolizable energy, and one macronutrient input. The predicted net energy is multiplied by the energy requirement for the companion animal to calculate feeding guidelines for the food for the companion animal. The calculated feeding guidelines are then displayed or provided to the owner of the companion animal, thereby deterring the owner from overfeeding the companion animal.

Reducing or eliminating the overfeeding of companion animals can assist in the maintenance of a healthy weight in, or reduced obesity of, companion animals, and a method of doing the same is also contemplated. The method comprises predicting the net energy provided by a food for the companion animal using a model consisting of the heat increment of feeding the food, expressed as a proportion of metabolizable energy, and one macronutrient input. The predicted net energy is multiplied by the energy requirement for the companion animal to calculate feeding guidelines for the food for the companion animal and the animal fed the food in accordance with the calculated guidelines.

BRIEF DESCRIPTION OF THE DRAWINGS

FIG. 1 is a graph of the energy expenditure per unit time taken from participants of the feeding study described in Example 1.

DETAILED DESCRIPTION

Net energy accounts for the proportion of energy expenditure attributed to the digestion, metabolism, and absorption of ingested food. Stated another way, while digestible energy or metabolizable energy both express potential energy, net energy expresses usable energy. Compared to metabolizable energy, which accounts for fecal and urinary energy losses, net energy is more complex to quantify.

Net energy (NE) models have been developed for use with multiple agricultural, production animal species such as swine and cattle, but to date, they do not exist for the companion animals. Further, the models developed for production animals not only require the input of the concentration of multiple nutrients, many of which are irrelevant in companion animal diets, but also, the feeding of production animals is subject to different economic and desired outcome pressures than the feeding of companion animals.

Net energy can be described as the metabolizable energy minus the heat increment of feeding (HIF). The heat increment of feeding, also commonly referred to as dietary-induced thermogenesis, is variable, and can be altered by dietary macronutrient content, diet processing conditions, and environmental temperature. The heat increment of feeding can be measured through indirect calorimetry, using measures of oxygen and carbon dioxide exchange to calculate energy expenditure of animals.

The net energy models provided herein, for the first time, easily estimate net energy values of companion animal diets. Though indirect calorimetry has previously been used to analyze energy expenditure, the models provided herein utilize heat increment of feeding as a proportion of metabolizable energy intake in companion animals. The provided models drastically alter, to positive effect, how dietary energy and the resultant feeding recommendations are determined for companion animals.

Example

Animals and Housing

All procedures were reviewed and approved by Procter & Gamble Pet Care's Institutional Animal Care and Use Committee and were in accordance with USDA and AAALAC guidelines (Study number: 013-9127; Protocol date: Mar. 7 2013). Nineteen domestic shorthair cats (10 males, 9 females) of similar age (4.3±0.48 yr) and body condition score (3.3±0.6 on a 9-point scale) were used. Cats were housed at the Pet Health and Nutrition Centre at Procter & Gamble Pet Care (Lewisburg, OH) and received physical exams by an accredited veterinarian to ensure health before and during the study. Cats had been appropriately acclimated to calorimetry chambers previous to the present study.

Cats were housed in free-living group environments with room enrichment including perches, toys, beds, scratching posts, and climbing apparatus. Cats could choose to go outside in a fully fenced area through a swinging door during daylight hours. The swinging door was locked from 16:00 to 07:00. The lighting schedule was 12 h:12 h light:dark beginning at 06:30. The housing room was equipped with a full wall of windows which provided cats with natural light. Room temperature was kept at 22° C., and relative humidity was 50 to 60%. Water was provided ad libitum via automatic waterers for the duration of the study. Surfaces, including walls and windows, were cleaned weekly with Nolvasan disinfectant (Allivet, St. Hialeah, FL) and daily cleaning was performed.

Experimental Diets and Design

Three diets were selected containing ingredients that are predicted to elicit high, medium, and low glycemic responses, and named based on their respective perceived glycemic response (PGR). The perceived glycemic response (PGR) refers to the expected glycemic response that would hypothetically result from consumption of each diet. This estimate was determined by accounting for the glycemic indexes of the main carbohydrate sources included in each diet, determined from studies in humans, and the glycemic response of these ingredients previously measured in companion animals. Three diets were studied, as shown in Table 1, below:

TABLE 1

Analyzed nutrient composition of the three experimental diets differing in perceived glycemic response (PGR)[1].

| Item | HighPGR[2] | MediumPGR[3] | LowPGR[4] |
|---|---|---|---|
| Moisture, % | 7.16 | 6.76 | 5.31 |
| Ash, % | 6.36 | 6.31 | 6.38 |

TABLE 1-continued

Analyzed nutrient composition of the three experimental diets
differing in perceived glycemic response (PGR)[1].

| Item | HighPGR[2] | MediumPGR[3] | LowPGR[4] |
|---|---|---|---|
| Crude protein[5], % | 38.02 | 35.86 | 42.06 |
| Ether extract, % | 15.7 | 22.2 | 22.9 |
| Crude fat, % | 10.83 | 20.02 | 20.42 |
| Nitrogen-free extract, % | 34.1 | 29.5 | 23.6 |
| Starch, % | 36.75 | 30.72 | 23.56 |
| Crude fiber, % | 1.17 | 1.78 | 2.58 |
| Acid detergent fiber, % | 1.88 | 2.95 | 2.43 |
| Neutral detergent fiber, % | 7.36 | 12.58 | 10.57 |

[1]Each diet was analyzed in triplicate. The perceived glycemic response (PGR) refers to the expected theoretical glycemic response that would result from consumption of each diet.
[2]HighPGR was Purina ONE Chicken and Rice (Nestle, St. Louis, MO) containing as main ingredients: chicken, brewer's rice, corn gluten meal, poultry by-product meal, wheat flour, animal fat preserved with mixed-tocopherols, whole grain corn, soy protein isolate, fish meal, animal liver flavor, KCl, H₃PO₄, CaCO₃, caramel color, choline chloride, and salt.
[3]MediumPGR was Iams Kitten Proactive Health (Procter & Gamble, Cincinatti, OH) containing as main ingredients: chicken, chicken by-product meal, corn meal, chicken fat preserved with mixed tocopherols, dried beet pulp, ground whole grain sorghum, dried egg product, natural flavor, fish oil preserved with mixed tocopherols, KCl, fructooligosaccharides, choline chloride, CaCO₃, brewer's dried yeast, DL-Met, and salt.
[4]LowPGR was Innova (Procter & Gamble, Cincinatti, OH) containing as main ingredients: turkey, chicken, chicken meal, whole grain barley and whole grain brown rice, chicken fat preserved with mixed tocopherols, peas, natural flavors, apples, herring, flaxseed, eggs, blueberries, pumpkin, tomatoes, sunflower oil, KCl, DL-Met, carrots, pears, cranberries, menhaden oil, cottage cheese, taurine, green beans, alfalfa sprouts, parsnips, and salt.
[5]Percentage N × 6.25.
[6]Calculated with modified Atwater equation (AAFCO, 1997): ME (kcal/kg) = 3.5 × CP (%) + 3.5 × carbohydrate (%) + 8.5 × crude fat (%).

Purina ONE Chicken and Rice was chosen as the High-PGR diet due to its high inclusion of Brewer's rice, known to elicit a high glycemic response. Jams Kitten Proactive health was comprised of ingredients including corn meal and sorghum, that both elicit a lower glycemic response than ingredients such as Brewer's rice. Last, Innova Dry Adult Cat Food was predicted to have the lowest perceived glycemic response (PGR) because of the use of barley, which has previously been found to elicit a low glycemic response, and its higher relative inclusion of protein.

Cats were assigned to diets based on a 3×3 Latin square with six complete squares and one incomplete square. Each period lasted 9 days with 8 days of adaptation to the diet, and 1 day of calorimetry measurements for 22 consecutive hours. Cats were fed to maintain body weight (BW) using individual historical data of energy intake and as shown in Table 2, below:

TABLE 2

Body weight and food and energy intake

| Variable | HighPGR | MedPGR | LowPGR | SEM[1] | P-Value |
|---|---|---|---|---|---|
| Body Weight (kg) | 4.99 | 4.95 | 4.94 | 0.34 | 0.99 |
| Food intake (g/day) | 45.6[a] | 37.9[b] | 40.0[b] | 2.68 | 0.02 |
| Calculated ME Intake (kcal/day) | 155.8 | 154.5 | 154.3 | 10.08 | 0.98 |

[a-c]Within a row, means without a common superscript differ (p < 0.05).
[1]Means were based on 19 cat observations per diet.

Cats were placed in individual cages for feeding at 07:00 each morning and given 60 minutes to eat before cats were removed and weighed. Dietary metabolizable energy (ME) was calculated using the modified Atwater calculation, and feed allowance was determined based on this estimation.
Chemical Analyses and Calculations Proximate analyses were completed in triplicate for each of the three experimental diets using AOAC procedures (AOAC, 1997). Ether extract was analyzed following acid hydrolysis (AOAC method 954.02), and dry matter (DM)

was determined by vacuum drying at 100° C. for 24 hours (AOAC method 934.01). Dietary nitrogen was determined by oxidation using a crude protein/nitrogen (CP/N) analyzer (AOAC method 990.03; Leco Corp., St Joseph, MI) and crude protein (CP) calculated. Crude fiber (CF) was analyzed through a ceramic fiber filtration method (AOAC method 962.09). Acid detergent fibre (AOAC method 973.18) and neutral detergent fibre (AOAC method 2002.04) were subsequently analyzed. Starch was determined using AOAC method 979.10. N-free extract (NFE), calculated as: NFE (%)=100−protein (%)−fat (%)−fiber (%)−ash (%)−moisture (%)

Ash was measured after exposure at 550° C. for 4 h (942.05), P through spectrophotometry (AOAC method 964.06), and Ca by atomic absorption spectrometry with electrothermal furnace (AOAC method 968.08).
Indirect Calorimetry On day 9 of each period, cats were placed in calorimetry chambers for a 22-hour measurement of respiratory gases. The calorimetry chambers (Qubit Systems, Kingston, ON, Canada) were composed of Plexiglas and measured 53.3× 53.3×76.2 cm. Each contained a shelf, feeder, water bowl, hammock, litter box, toy, and free area with a fleece bed. Water was given freely from water bowls. The chambers were large enough to provide enough separation between areas used for feeding, sleeping and elimination. Daily, the chambers and water bowls were disinfected and the litter, litter boxes, toys, hammock, and beds were removed and cleaned.

On study days, cats were placed in respiration calorimetry chambers and after 30 min of gas equilibration, two fasting respiration calorimetry measurements were taken on each cat at 60 and 30 min prior to feeding to establish fasted resting $CO_2$ ($VCO_2$) production and $O_2$ consumption ($VO_2$). After the second fasting measurement, cats were fed their individual assigned diet. Thereafter, $VO_2$ and $VCO_2$ were measured in 30 min intervals. The calorimeter is open circuit and ventilated with room air being drawn through at a rate between 5 and 10 L/min depending on the weight of individual cats which was used to calculate total volume.

Calibration of the analyzers and mass flow meters was performed prior to each day of calorimetry measurements and continued every 12 hours during the study or whenever a drift of >5% was observed on the half-hourly reference channel. Calibration was performed using standard gas mixtures of N and a span gas containing 1.012% $CO_2$. After 22 hours, the cats were removed from chambers and placed back into their rooms.
Analyses Levels of $O_2$ and $CO_2$ in the respiratory chambers were measured with infrared $O_2$ and $CO_2$ analyzers (Qubit Systems, Kingston, ON, Canada). Rate of airflow was measured using a mass flow meter to calculate total volume.

Energy expenditure (EE) was segmented by time point. Fasted measurements were taken 60 and 30 minutes prior to feeding. Postprandial energy expenditure (EE), fed energy expenditure (EE), return to fasted energy expenditure (EE), and late fasted energy expenditure (EE) were measured at 30 minute intervals between 0 to 5.5 hours, 5.5 to 10.5 hours, 10.5 to 15.5 hours, and 15.5 h to 21 hours post feeding, respectively. Since a clear increase in energy expenditure (EE) was observed between 0 and 2 hours, the average energy expenditure (EE) during the first 2 hours post feeding was also analyzed. These measurements are shown in FIG. 1, wherein the cats were fed at t=0 minutes and vertical dotted lines separating fasted, immediate posptandial, post-prandial, fed, return to fasted, and late fasted time points, respectively.

In the present study, resting fed metabolic rate (RFMR) was used to approximate basal metabolic rate (BMR). The resting fed metabolic rate is defined as the lowest observed value of energy expended by an animal in a fed state that otherwise meets the criteria for basal metabolism.

Calculations

Energy expenditure was calculated by measuring $CO_2$ production and $O_2$ consumption as follows:

$$EE(kcal/d)=[3.94\times O2exchange\ (L/h)+1.11\times CO2\ exchange\ (L/h)]\times 24h$$

The net energy of the diets was calculated as the metabolizable energy per 100 g dry matter, minus heat increment of feeding (HIF) associated with consuming the same amount of food. Heat increment of feeding was calculated for the first 2 h post feeding and the entire calorimetry period (2-21 h), as the difference in area under the curve of postprandial energy expenditure minus the resting fed metabolic rate. Area under the curve (AUC) was calculated using the linear trapezoidal rule. Net energy was highest for the LowPGR diet, followed by the Medium and HighPGR diets (P<0.001).

Modeling Net Energy and Statistical Analyses

Correlations between calculated net energy and analyzed metabolizable energy were performed using PROC CORR in SAS version 9.4. Net energy models were developed using both the Heat Increment of Feeding from 0-2 h postprandial, and the heat increment of feeding for the complete calorimetry period (0-21 h). Coefficients chosen minimized residual sum of squares between predicted and calculated net energy. Coefficients of determination ($R^2$) and rMSPE values were calculated in Microsoft Excel (2017) and numerically compared to evaluate the fit of each model to the observed data.

Using SAS version 9.3, statistical power of was calculated for energy expenditure and was determined to be 97.4% for the studied population of 19 cats. Body weight, feed intake, and heat increment of feeding data were analyzed using the PROC MIXED of SAS (Version 9.3, SAS Institute Inc., Cary, NC, USA) with individual cats as the experimental unit, cat and period as the random effects, and diet as the fixed effect. Repeated measures analyses were performed for Energy Expenditure over time using the Compound Symmetry covariance structure, as it had the lowest area under the curve (AUC). Energy expenditure was pooled from all diets, and differences in Energy Expenditure across time were compared against fasted Energy expenditure (time=−30), using the Dunnett test (SAS Version 9.4). Estimates were separated using the difference of least squares means. An alpha of 0.05 was used to declare statistical significance. Data were reported as least-squares means±SEM.

In period 2, data was not recorded past the 10.5 h calibration for 4 cats due to software malfunction. Two of these cats were fed the LowPGR diet, one was fed the MediumPGR diet, and one was fed the HighPGR diet. The data that was collected in the 12 h previous to calibration was included in the analyses. In period 3, the calorimetry software did not record the first 12 h of data for one cat fed the LowPGR diet. Data from this cat was not included for heat increment of feeding calculation.

Diet Composition, Body Weight and Feed Intake

The composition of the three test diets differed in macronutrient content as shown above in Table 1. Over the duration of the study, body weight did not differ among dietary treatments (P>0.05). On an as-fed basis, daily food intake was higher for the HighPGR treatment (45.6±2.7 g/d) than the MediumPGR (37.9±2.7 g/d) and LowPGR treatments (40.0±2.7 g/d) (Table 2; P=0.02). However, metabolizable energy (ME) intake did not differ between diets (P=0.98).

Indirect Calorimetry Results

Following feeding, energy expenditure (EE) increased until 1.5 hours, decreased between 2 and 4 hours, remained constant until 20.5 hours, then increased until the end of the calorimetry period (P<0.05; FIG. 1). In the fasted state (−1 to 0 hours), energy expenditure did not differ between dietary treatments (P=0.166). There were no differences in resting fed metabolic rate (RFMR) between dietary treatments (P=0.89). In the first 2 hours postprandial, energy expenditure was not different between dietary treatments (P=0.148). In the postprandial state (0 to 5.5 hours), energy expenditure did not differ between dietary treatments (P=0.167). In the fed state (5.5 to 10.5 hours), energy expenditure was higher in cats fed the High and MediumPGR diets as compared to cats fed the LowPGR diet (P<0.001). In the return to fasted state (10.5-15.5 hours), energy expenditure was higher in cats fed the HighPGR diet than cats fed the Medium and LowPGR diets (Table 3; P=0.04). In the late fasted state (15.5-21 hours), energy expenditure was highest in cats fed the HighPGR diet, intermediate in cats fed the MediumPGR diet, and lowest in those fed the LowPGR diet (P<0.001). Over 21 hours, energy expenditure was highest in cats fed the HighPGR diet, intermediate in cats fed the MediumPGR diet, and lowest in cats fed the LowPGR diet (P<0.001).

TABLE 3

Indirect calorimetry measurements. Fasting measurements were taken at t = −60 and t = −30 min, and fed measurements were taken at t = 0 min onward.

| Variable | HighPGR | MedPGR | LowPGR | SEM[1] | P-value |
|---|---|---|---|---|---|
| EE (kcal/kg*d⁻¹) | | | | | |
| RFMR[2] | 36.5 | 36.1 | 35.4 | 2.18 | 0.89 |
| Overall (0-21 h) | 43.3$^a$ | 42.4$^b$ | 41.5$^c$ | 1.56 | <0.001 |
| Fasted (−1-0 h) | 42.1 | 40.9 | 39.8 | 1.82 | 0.166 |
| Postprandial (0-5.5 h) | 41.7 | 41.5 | 40.7 | 1.54 | 0.167 |
| Immediate Postprandial (0-2 h) | 43.4 | 44.5 | 42.4 | 1.78 | 0.148 |
| Fed (5.5-10.5 h) | 42.2$^a$ | 41.1$^a$ | 39.9$^b$ | 1.42 | <0.001 |
| Return to Fasted (10.5-15.5 h) | 44.7$^a$ | 43.8 $^b$ | 43.5 $^b$ | 1.49 | 0.04 |
| Late Fasted (15.5-21 h) | 44.1$^a$ | 43.1$^b$ | 42.0$^c$ | 1.63 | <0.001 |

$^{a-c}$Within a row, means without a common superscript differ (p < 0.05).
[1]Means were based on 18 cat observations per diet.
[2]RFMR: resting fed metabolic rate.

For the first 2 hours postprandial, the heat increment of feeding (HIF) per 100 g of diet (DM basis) was higher for MediumPGR than the Low and HighPGR dietary treatments (Table 4; P<0.001). For the complete calorimetry period (0-21 hours), the heat increment of feeding (HIF) per 100 g of diet on a DM basis did not differ among dietary treatments (P=0.127). Over the first 2 h postprandial, heat increment of feeding (HIF) amounted to 1.58%, 2.03% and 1.60% of metabolizable energy (ME) intake for the High, Medium and LowPGR diets, respectively, and did not differ among dietary treatments (P=0.13; Table 4). Over the whole calorimetry period, (0-21 h) the heat increment of feeding (HIF) was 21.7%, 21.6% and 19.5% of metabolizable energy (ME)

intake for the High, Medium and LowPGR diets, respectively, and did not differ among dietary treatments (Table 4).

TABLE 4

Metabolizable energy (ME) and heat increment used to determine NE/100 g diet. Heat increment of feeding (HIF) is presented as area under the curve (AUC) from 0-2 hours postprandial, and 0-21 hours postprandial.

| Name | HighPGR | MedPGR | LowPGR | SEM[2] | P-Value |
|---|---|---|---|---|---|
| ME, kcal/100 g diet (DM)[1] | 458.9[c] | 490.6[b] | 505.5[a] | 3.85 | <0.001 |
| $HIF_{(0-2\ h)}$ | | | | | |
| HIF (% of ME) | 1.58 | 2.03 | 1.60 | 0.25 | 0.13 |
| HIF, kcal/100 g diet (DM) | 5.82[a] | 8.87[a] | 6.56[b] | 1.00 | <0.001 |
| Measured NE, kcal/100 g diet (DM) | 453.03[c] | 481.7[b] | 499.0[a] | 1.00 | <0.001 |
| $HIF_{(0-21\ h)}$ | | | | | |
| HIF (% of ME) | 21.7 | 21.6 | 19.5 | 2.15 | 0.50 |
| HIF, kcal/100 g diet (DM) | 77.6 | 94.6 | 79.3 | 9.20 | 0.127 |
| Measured NE, kcal/100 g diet (DM) | 381.3[c] | 396.0[b] | 426.3[a] | 9.20 | <0.001 |

[a-c]Within a row, means without a common superscript differ (p < 0.05).
[1]DM = dry matter
[2]Means were based on 18 cat observations per diet.

Net Energy Models

Net energy models were created with heat increment of feeding values taken from 0-2 hours (Table 5; equations 1-4), and 0-21 hours (Table 5; equations 5-8). Models developed using the heat increment of feeing (HIF) values from 0-2 hours more closely predicted analyzed net energy (NE) compared to models developed using the heat increment of feeing (HIF) values from 0-21 hours. Of the eight suggested models to predict net energy (NE), the model net energy (NE)=(0.941×metabolizable energy (ME))+(0.519× crude protein (CP)) had the highest $R^2$ and lowest rMSPE. Of the various macronutrient inputs used to model net energy, including crude protein as a variable maximized accuracy of the model.

TABLE 5

Proposed net energy (NE) models and associated $R^2$ and rMSPE using heat increment of feeding (HIF) values from 0-2 hours postprandial, and 0-21 hours postprandial.

| Proposed Model[1] | | $R^2$ | rMSPE |
|---|---|---|---|
| Using $HIF_{(0-2\ h)}$ | 1. NE = (0.941 × ME) + (0.519 × CP) | 0.975 | 2.97 |
| | 2. NE = (0.992 × ME) − (0.170 × CL) | 0.973 | 3.14 |
| | 3. NE = (0.995 × ME) − (0.0002 × Starch) | 0.972 | 3.21 |
| | 4. NE = (0.984 × ME) + (0.246 × CF) | 0.972 | 3.21 |
| Using $HIF_{(0-21\ h)}$ | 5. NE = (0.605 × ME) + (2.60 × CP) | 0.337 | 25.1 |
| | 6. NE = (0.843 × ME) − (0.431 × CL) | 0.283 | 27.1 |
| | 7. NE = (0.826 × ME) − (0.0001 × Starch) | 0.294 | 27.0 |
| | 8. NE = (0.800 × ME) + (6.386 × CF) | 0.296 | 26.9 |

[1]Energy in kcal/kg dry matter, nutrients in g/kg dry matter; (CP: crude protein, CL: crude lipids, CF: crude fiber).

Energy expenditure was calculated by measuring $CO_2$ production and $O_2$ consumption. Net energy was determined as the difference between metabolizable energy of the diets and the heat increment of feeding. Net energy was highest for the LowPGR diet, followed by the Medium and High-PGR diets (P<0.001).

Models created using the heat increment of feeding values from 0-2 hours correlated better to the data than those from 0-21 hours (equations 4-8 in Table 5, above). It is believed that this observation may be a result of the particularly nutrient metabolism of cats, i.e., that the costs associated with protein metabolism are higher relative to other macronutrients and/or that cats increases protein oxidation or deposition at the end of the calorimetry period. Regardless, the observed increase in energy expenditure at the end of the calorimetry period appears to be a characterizing feature of cat nutrient metabolism in general, as it was consistently observed among all diets, and these models are thus believed to provide a more accurate representation of the available energy in a food for a companion animal than, e.g., the traditional or modified Atwater equations.

Results

The observed measurements of energy expenditure were within the ranges expected by those of ordinary skill in the art. In cats fed both high fat and high carbohydrate diets, fasted energy expenditure is known to range from 44-47 kcal/kg/d, and fed energy expenditure is known to range from 43-51 kcal/kg/d. Furthermore, daily resting energy expenditure in cats is known to be about 36+/−7.7 kcal/kg/day with underweight, normal and overweight body condition scores. Furthermore, the duration of observed postprandial energy expenditure increase in the present study is similar to that known to be exhibited by other species, both monogastrics and ruminants. Finally, when heat increment of feeding was taken from 0-21 hours and expressed as a proportion of metabolizable energy, the present results were comparable to known those known to exist in other mammals.

These similarities suggest that the above results and models are valid, and appropriate to use to predict net energy for companion animals, in general and domestic cats in particular.

This example shows that net energy, which accounts for energy spent in the digestion, absorption and metabolism of nutrients, is a more accurate measure of energy directly available to an animal than metabolizable energy (ME), digestible energy (DE) or gross energy (GE). Expressing energy density on a net energy basis could allow a more accurate feeding recommendation that what is currently utilized for commercial feeding recommendations, and limit the provision of excess calories to companion animals. Of additional benefit is that the provided models to estimate net energy may be based upon a lower number of parameters than are required in either the traditional or modified Atwater equation. The model(s) provided are thus not only more accurate than conventional models based upon metabolizable energy (ME), but are also simplified compared to such existing models.

What is claimed is:

1. A method of providing feeding guidelines for a food for reducing obesity in a cat comprising:

feeding the cat a first amount of the food;

measuring respiratory gases emitted by the cat in 30-minute intervals over a postprandial time period of 0-2 hours;

determining an energy expenditure of the cat from the emitted respiratory gases over the postprandial time period of 0-2 hours;

determining a heat increment of feeding the first amount of the food from the determined energy expenditure of the cat over the postprandial time period of 0-2 hours;

generating a model consisting of the determined heat increment of feeding the first amount of the food over the postprandial time period of 0-2 hours, expressed as a proportion of metabolizable energy, and one crude protein input, wherein the model is net energy=(0.941× metabolizable energy (ME))+(0.519×crude protein (CP));

predicting, using the model, a net energy provided by the first amount of the food;

determining feeding guidelines for the food for reducing obesity in the cat by multiplying the predicted net energy by an energy requirement for the cat;

providing the feeding guidelines for reducing obesity in the cat on a packaging of the food; and repeatedly feeding the cat a second amount of the food in accordance with the provided feeding guidelines for reducing obesity in the cat.

2. The method of claim 1, wherein the energy requirement for the cat is 24-35 kcal/lb body weight/day.

3. A method of packaging a food for reducing obesity in a cat comprising:

providing a food for the cat and packaging therefor;

feeding the cat a first amount of the food;

measuring respiratory gases emitted by the cat in 30-minute intervals over a postprandial time period of 0-2 hours;

determining an energy expenditure of the cat from the emitted respiratory gases over the postprandial time period of 0-2 hours;

determining a heat increment of feeding the first amount of the food from the determined energy expenditure of the cat over the postprandial time period of 0-2 hours;

generating a model consisting of the determined heat increment of feeding the first amount of the food over the postprandial time period of 0-2 hours, expressed as a proportion of metabolizable energy, and one crude protein input, wherein the model is net energy=(0.941× metabolizable energy (ME))+(0.519×crude protein (CP));

predicting, using the model, a net energy provided by the first amount of the food;

multiplying the predicted net energy by an energy requirement for the cat to provide feeding guidelines for the food for reducing obesity in the cat;

printing the feeding guidelines for reducing obesity in the cat on the packaging;

packaging the food in the printed packaging; and repeatedly feeding the cat a second amount of the food in accordance with the feeding guidelines for reducing obesity in the cat printed on the printed packaging.

\* \* \* \* \*